(12) United States Patent
Rallapalli et al.

(10) Patent No.: US 11,472,756 B2
(45) Date of Patent: Oct. 18, 2022

(54) METHOD OF SEPARATING LINEAR ALPHA OLEFINS

(71) Applicant: SABIC GLOBAL TECHNOLOGIES B.V., Bergen op Zoom (NL)

(72) Inventors: Jagan Mohan Rallapalli, Riyadh (SA); Shahid Azam, Riyadh (SA); Haresh Shakralal Patel, Ahmedabad (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 10 days.

(21) Appl. No.: 16/470,818

(22) PCT Filed: Dec. 19, 2017

(86) PCT No.: PCT/IB2017/058158
§ 371 (c)(1),
(2) Date: Jun. 18, 2019

(87) PCT Pub. No.: WO2018/116177
PCT Pub. Date: Jun. 28, 2018

(65) Prior Publication Data
US 2019/0345080 A1 Nov. 14, 2019

Related U.S. Application Data

(60) Provisional application No. 62/436,293, filed on Dec. 19, 2016.

(51) Int. Cl.
*C07C 7/04* (2006.01)
*B01D 3/32* (2006.01)
(Continued)

(52) U.S. Cl.
CPC .............. *C07C 7/04* (2013.01); *B01D 3/141* (2013.01); *B01D 3/143* (2013.01); *B01D 3/322* (2013.01); *C07C 11/02* (2013.01)

(58) Field of Classification Search
None
See application file for complete search history.

(56) References Cited

U.S. PATENT DOCUMENTS 4,886,933 A * 12/1989 Shiraki ..................... C07C 2/30
585/522
2014/0012059 A1 * 1/2014 Vinel ..................... C07C 7/005
585/809

FOREIGN PATENT DOCUMENTS

| CN | 1427832 | 7/2003 |
| CN | 1469765 | 1/2004 |

(Continued)

OTHER PUBLICATIONS

Nag, Ashis "Distillation Practices" Distillation and Hydrocarbon Processing Practices. 2016. pages 1-113. (Year: 2016).*

(Continued)

*Primary Examiner* — Philip Y Louie
*Assistant Examiner* — Alyssa L Cepluch
(74) *Attorney, Agent, or Firm* — Norton Rose Fulbright US LLP (57) ABSTRACT

A method of separating linear alpha olefins includes: passing a feed stream comprising linear alpha olefins through a first column; distributing a C8− fraction to a top portion of the first column; distributing a C9+ fraction to a bottom portion of the first column; passing the C8− fraction directly to a top portion of a second column; passing the C9+ fraction directly to a bottom portion of a second column; distributing a C11+ fraction to the bottom portion of the second column; withdrawing a C10 fraction as a side draw from the second column; and passing a liquid stream and a vapor stream from the second column to the first column.

13 Claims, 2 Drawing Sheets

(51) Int. Cl.
  *B01D 3/14* (2006.01)
  *C07C 11/02* (2006.01)

(56) References Cited

FOREIGN PATENT DOCUMENTS

| | | |
|---|---|---|
| CN | 101717657 | 6/2010 |
| CN | 101774877 | 7/2010 |
| EP | 2738151 A1 | 6/2014 |

OTHER PUBLICATIONS

John Wiley & Sons "Olefins-Higher" Wiley Critical Content-Petroleum Technology, vol. 1-2. 2007. pages 1028-1046 (Year: 2007).*

Distillation Tutorial II: McCabe-Thiele Method of Distillation Design pp. 1-8. 2015 https://personal.egr.uri.edu/lucia/tutorials/tutorial2.html (Year: 2015).*

Emtir, M. et al. "Rigorous simulation of energy integrated and thermally coupled distillation schemes for ternary mixture", Applied Thermal Engineering, 2001, vol. 21, pp. 1299-1317.

International Search Report for International Application No. PCT/IB2017/058158, International Filing Date Dec. 19, 2017, dated Mar. 26, 2018, 5 pages.

Written Opinion for International Application No. PCT/IB2017/058158, International Filing Date Dec. 19, 2017, dated Mar. 26, 2018, 6 pages.

Zhai, J. et al. "Applications of dividing wall column technology to industrial-scale cumene production", Chemical Engineering Research and Design, 2015, vol. 102, pp. 138-149.

Office Action issued in counterpart Chinese Patent Application No. 201780078428X, dated Jan. 27, 2021.

Hung Bin et al. *Organic Chemistry*. Chemical Industry Press, 1980.

Mengzheng et al. *Principles of Fine Chemical Products Synthesis*. Sinopec Press, p. 85, 2000.

Office Action issued in Corresponding Chinese Application No. 201780078428.X, dated Sep. 2, 2021 (English Translation provided).

Xuzhi et al. *Ethylene Derivatives Engineering*. Chemical Industry Press, p. 385, 1995.

* cited by examiner

METHOD OF SEPARATING LINEAR ALPHA OLEFINS

CROSS REFERENCE TO RELATED APPLICATIONS

This application is a National Stage application of PCT/IB2017/058158, filed Dec. 19, 2017, which claims the benefit of U.S. Application No. 62/436,293, filed Dec. 19, 2016, both of which are incorporated by reference in their entirety herein.

BACKGROUND

Linear olefins are one of the most useful classes of hydrocarbons used as raw materials in the petrochemical industry. Among these linear alpha-olefins, unbranched olefins whose double bond is located at a terminus of the chain, form an important subclass. Linear alpha olefins can be converted to linear primary alcohols by hydroformylation. Hydroformylation can also be used to prepare aldehydes as the major products, which in turn can be oxidized to afford synthetic fatty acids, especially those with an odd carbon number, useful in the production of lubricants. Linear alpha olefins are also used in the most important class of detergents for domestic use, namely the linear alkylbenzene sulfonates, which are prepared by Friedel-Crafts reaction of benzene with linear olefins followed by sulfonation.

Although linear olefins are the product of dehydrogenation of linear alkanes, the major portion of such products consists of the internal olefins. Preparation of alpha olefins is based largely on oligomerization of ethylene, which has a corollary that the alpha-olefins produced have an even number of carbon atoms. Oligomerization processes for ethylene are based mainly on organoaluminum compounds or transition metals as catalysts.

Oligomerization methods for preparing linear alpha-olefins are widely known in the art. These methods are typically carried out in the presence of a catalyst, preferably comprising a zirconium component, such as zirconium tetraisobutyrate, and an aluminum component as activator, such as ethyl aluminum sesquichloride.

Typically, the effluent from the reactor used to produce the linear alpha olefins is directed to one or more distillation columns to separate the various fractions of linear alpha olefins. One problem associated with the recovery of various fractions of produced linear alpha olefins includes impurities, such as solvents and catalysts, contaminating the various fractions. For example, under certain conditions, such as during a plant startup or feed flow interruptions, the amount of impurities in the $C_4$ and $C_6$ streams may reach up to 10,000 parts per million. As a result, the isolated fractions are off-specification (i.e., do not meet market demands of purity) and cannot be used without further purification.

In the production of linear alpha olefins, distillation columns are used to separate light hydrocarbons, for example, ethylene and butane, from heavier hydrocarbons. These separation processes present many engineering challenges. For example, a stream of linear alpha olefins produced by the oligomerization of ethylene can comprise C4-C20 straight chain hydrocarbon molecules. These linear alkenes can serve as building blocks in a wide range of industrial applications. For example, linear alkenes can serve as co-monomers, plasticizers, lubricants and stabilizers. Accordingly, the separation of these olefins from an oligomerization reactor product stream remains a commercially important goal. Furthermore, it is important that these products are of a high purity level that can meet industry quality standards.

Starting with light hydrocarbons such as butane, linear alkenes are often separated using a series of distillation columns. For example, decene (C10) can be separated from a hydrocarbon stream that comprises octane, decene, dodecene and other higher alkenes. The narrow range of boiling points and relative volatilities of the components in the stream make separation by conventional distillation difficult and energy intensive. For example, decene is often separated from this stream using a direct sequence of two distillation columns in series. Each of the distillation columns in this direct sequence comprises both a reboiler and a condenser. As a result, the direct sequence consumes a high and undesirable amount of energy, for example, the columns can demand a high reboiler duty and a high condenser duty.

Thus, there is a need for an efficient method of separating linear alpha olefins that can significantly reduce energy consumption, maintain product flow, increase product purity, and simplify the overall separation process.

SUMMARY

Disclosed, in various embodiments, are methods of separating linear alpha olefins.

A method of separating linear alpha olefins, comprises: passing a feed stream comprising linear alpha olefins through a first column; distributing a C8− fraction to a top portion of the first column; distributing a C9+ fraction to a bottom portion of the first column; passing the C8− fraction directly to a top portion of a second column; passing the C9+ fraction directly to a bottom portion of a second column; distributing a C11+ fraction to the bottom portion of the second column; withdrawing a C10 fraction as a side draw from the second column; and passing a liquid stream and a vapor stream from the second column to the first column.

A method of separating linear alpha olefins, comprises: passing a feed stream comprising linear alpha olefins through a column configuration, wherein passing the feed stream through the column configuration comprises: passing the feed stream through a first column; distributing a fraction A to a top portion of the first column; distributing a fraction C to a bottom portion of the first column; withdrawing a side stream from a middle portion of the first column; passing the side stream to a middle portion of a second column; withdrawing a recycle stream from a top portion of the second column; passing the recycle stream to the top portion of the first column; and distributing a fraction B to a bottom portion of the second column.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Disclosed herein is a method that can provide an efficient method of separating linear alpha olefins that can significantly reduce energy consumption, increase product purity, and simplify the overall separation process. For example, the method disclosed herein can reduce energy consumption by greater than or equal to 20%. The present method can reduce the total reboiler duty and the total condenser duty for the process. The present method can reduce the total number of required heat exchanges needed for separation. The present method can provide product purity levels greater than or equal to 99 weight % (wt. %), for example, a decene product of greater than or equal to 99.5 wt. % purity can be produced. The present method can also reduce overall costs, equipment, and maintenance needs.

In the production of linear alpha olefins, the linear alkanes beginning with butane are generally in a series of distillation columns. Decene (C10) is generally separated from the stream that contains octane, decene, do-decene, and higher alkenes. In the disclosed method, a reboiler and condenser are by-passed and instead, feed is introduced where the reboiler and condenser would be. With these modifications, it was surprisingly discovered that the desired purity levels can be achieved and energy consumption can also be reduced by less than or equal to 20% for the reboiler.

The method disclosed herein for separating linear alpha olefins can include a modified sequence of distillation columns for the isolation of decene. For example, the method can include passing a C8− fraction of linear alpha olefins directly from a top portion of a first column to a top portion of a second column. Accordingly, the present method can bypass a first column condenser. The present method can include passing a C9+ fraction directly from the bottom portion of a first column to a bottom portion of a second column. Accordingly, the present method can bypass a first column reboiler. A liquid stream and vapor stream can be recycled from the second column back to the first. A purified decene product stream can be withdrawn as a side draw from the second column. Accordingly, the present method can reduce equipment needs and reduce total energy requirements.

The method can include passing a feed stream through a column, for example, a first distillation column. The feed stream can comprise hydrocarbons, for example, C4-C20 linear alpha olefins. For example, the source of the feed stream can be the product of a linear alpha olefin production process, for example, ethylene oligomerization. The feed stream can also comprise a solvent, for example, toluene, as well as spent catalyst particles and catalyst deactivating agents.

"Ethylene oligomerization" combines ethylene molecules to produce linear alpha-olefins of various chain lengths with an even number of carbon atoms. This approach results in a distribution of alpha-olefins. Oligomerization of ethylene can produce 1-hexene.

1-Hexene is commonly manufactured by two general routes: (i) full-range processes via the oligomerization of ethylene and (ii) on-purpose technology. A minor route to 1-hexene, used commercially on smaller scales, is the dehydration of hexanol. Prior to the 1970s, 1-hexene was also manufactured by the thermal cracking of waxes. Linear internal hexenes were manufactured by chlorination/dehydrochlorination of linear paraffins.

Fischer-Tropsch synthesis to make fuels from synthesis gas derived from coal can recover 1-hexene from the aforementioned fuel streams, where the initial 1-hexene concentration cut can be 60% in a narrow distillation, with the remainder being vinylidenes, linear and branched internal olefins, linear and branched paraffins, alcohols, aldehydes, carboxylic acids, and aromatic compounds. The trimerization of ethylene by homogeneous catalysts has been demonstrated.

There are a wide range of applications for linear alpha olefins. The lower carbon numbers, 1-butene, 1-hexene and 1-octene can be used as comonomers in the production of polyethylene. High density polyethylene (HDPE) and linear low density polyethylene (LLDPE) can use approximately 2-4% and 8-10% of comonomers, respectively.

Another use of $C_4$-$C_8$ linear alpha olefins can be for production of linear aldehyde via oxo synthesis (hydroformylation) for later production of short-chain fatty acid, a carboxylic acid, by oxidation of an intermediate aldehyde, or linear alcohols for plasticizer application by hydrogenation of the aldehyde.

An application of 1-decene is in making polyalphaolefin synthetic lubricant base stock (PAO) and to make surfactants in a blend with higher linear alpha olefins.

C10-C14 linear alpha olefins can be used in making surfactants for aqueous detergent formulations. These carbon numbers can be reacted with benzene to make linear alkyl benzene (LAB), which can be further sulfonated to linear alkyl benzene sulfonate (LABS), a popular relatively low cost surfactant for household and industrial detergent applications.

Although some C14 alpha olefin can be sold into aqueous detergent applications, C14 has other applications such as being converted into chloroparaffins. A recent application of C14 is as on-land drilling fluid base stock, replacing diesel or kerosene in that application. Although C14 is more expensive than middle distillates, it has a significant advantage environmentally, being much more biodegradable and in handling the material, being much less irritating to skin and less toxic.

C16-C18 linear olefins find their primary application as the hydrophobes in oil-soluble surfactants and as lubricating fluids themselves. C16-C18 alpha or internal olefins are used as synthetic drilling fluid base for high value, primarily off-shore synthetic drilling fluids. The preferred materials for the synthetic drilling fluid application are linear internal olefins, which are primarily made by isomerizing linear alpha-olefins to an internal position. The higher internal olefins appear to form a more lubricious layer at the metal surface and are recognized as a better lubricant. Another application for C16-C18 olefins is in paper sizing. Linear alpha olefins are, once again, isomerized into linear internal olefins are then reacted with maleic anhydride to make an alkyl succinic anhydride (ASA), a popular paper sizing chemical.

C20-C30 linear alpha olefins production capacity can be 5-10% of the total production of a linear alpha olefin plant. These are used in a number of reactive and non-reactive applications, including as feedstocks to make heavy linear alkyl benzene (LAB) and low molecular weight polymers used to enhance properties of waxes.

The use of 1-hexene can be as a comonomer in production of polyethylene. High-density polyethylene (HDPE) and linear low-density polyethylene (LLDPE) use approximately 2-4% and 8-10% of comonomers, respectively.

Another use of 1-hexene is the production of the linear aldehyde heptanal via hydroformylation (oxo synthesis). Heptanal can be converted to the short-chain fatty acid heptanoic acid or the alcohol heptanol.

A pressure within the first column can be 0 kiloPascals to 1000 kiloPascals, for example, 50 kiloPascals to 500 kiloPascals, for example, 100 kiloPascals to 250 kiloPascals, for example, 130 kiloPascals. A temperature within the first column can be −100° C. to 300° C., for example, −40° C. to 240° C., for example, 0° C. to 175° C., for example, 155° C.

A C8− fraction can be distributed to and withdrawn from a top portion of the first column. For example, the C8− fraction can be passed directly from the top portion of the first column to a top portion (for example, a stage 10) of a second distillation column. For example, the C8− fraction can bypass a condenser and reflux drum for the first column. A C9+ fraction can be distributed to and withdrawn from a bottom portion of the first column. The C9+ fraction can be passed directly from the bottom portion of the first column to a bottom portion (for example, a stage 30) of the second distillation column. For example, the C9+ fraction can bypass a reboiler for the first column.

A pressure within the second column can be 0 kiloPascals to 1000 kiloPascals, for example, 50 kiloPascals to 500 kiloPascals, for example, 100 kiloPascals to 250 kiloPascals, for example, 120 kiloPascals. A temperature within the second column can be −100° C. to 300° C., for example, −40° C. to 240° C., for example, 0° C. to 150° C., for example, 127° C.

A top product, for example, a C8− fraction, can be distributed to and withdrawn from a top portion of the second column. The C8− fraction can be passed through a heat exchanger. The heat exchanger can be a condenser that cools a portion of the C8− fraction. For example, the heat exchanger can partially condense at least a portion of the C8− fraction. The heat exchanger can be any heat exchanger suitable for cooling. For example, the heat exchanger can include a spiral heat exchanger and/or a plate heat exchanger. For example, the heat exchanger can utilize a stream of coolant fluid as a cooling means. The C8− fraction can then be passed through a reflux drum. A portion of the C8− fraction can be recycled back to a top portion of the second distillation column as a reflux stream. The remaining portion of the C8− fraction can be withdrawn as a product stream. A mole to mole (mol/mol) reflux ratio for the second column can be 3:1 to 4:1, for example, 3.6:1 to 3.9:1, for example, 3.792. The condenser duty for the second column can be less than or equal to 2000 kiloWatts (kW), for example, less than or equal to 1500 kW, for example, less than or equal to 1300 kW, for example less than or equal to 1285 kW, for example, 1283.44 kW.

A C10 fraction can be withdrawn from the second distillation column as a side draw. For example, the C10 fraction can comprise decene. For example, the C10 fraction can comprise greater than or equal to 99 wt. % decene, for example, greater than or equal to 99.5 wt. % decene. A flow rate for the C10 fraction can be greater than or equal to 2000 kilograms per hour (kg/hr), for example, greater than or equal to 2200 kg/hr, for example, 2216 kg/hr. A temperature for the C10 fraction can be 100° C. to 300° C., for example, 177° C.

A bottom product, for example, a C11+ fraction, can be distributed to and withdrawn from a bottom portion of the second distillation column. For example, a temperature for the C11+ fraction can be 100° C. to 300° C., for example, 245° C. A reboiler stream can be withdrawn from a bottom portion of the second column. The reboiler stream can be passed through a heat exchanger, for example, a reboiler. The reboiler stream can then be recycled back to the bottom portion of the second distillation column. A mol/mol boil-up ratio for the second column can be 4:1 to 5:1, for example, 4.2:1 to 4.4:1, for example, 4.349. A reboiler duty for the second column can less than or equal to 1500 kw, for example, less than or equal to 1300 kW. The energy from the reboiler can be used for both the first column and the second column.

A liquid stream can be recycled from a top portion (for example, a stage 9) of the second column back to a top portion of the first column. A vapor stream can be recycled from a bottom portion (for example, a stage 30) of the second column back to a bottom portion of the first column. The first column and second column can comprise a total of 50 to 100 stages, for example, 60 to 70 stages, for example, 64 total stages. The present method can further comprising passing the C8− fraction and/or the C11+ fraction through additional columns, for example, a third column, for further downstream processing.

The vapor streams and liquid streams can be controlled for the optimization of the system. For example, the distillation columns can comprise multiple electrical controllers in various locations. The distillation columns can also comprise multiple control valves. For example, the distillation columns can comprise temperature controllers, pressure controllers, level controllers, flow valves, pressure valves, or a combination comprising at least one of the forgoing. The distillation columns can also comprise various combinations of controllers and valves in communication with each other.

Linear alpha olefin fractions generally are separated using a sequence of distillation columns in series, wherein a condenser is used in each column. In the disclosed method, fractions are separated using a modified configuration of two distillation columns in series. A side stream is withdrawn from a middle portion of a first column and then passed to a middle portion of a second column. A recycle stream is also withdrawn from a top portion of the second column and passed directly back to a top portion of the first column. The utilization of the side stream and the recycle stream in this modified configuration can allow the second column to operate without a condenser. A fraction "A" can be withdrawn from a top portion of the first column. A fraction "B" can be withdrawn from a bottom portion of the second column. A fraction "C" can be withdrawn from a bottom portion of the first column. It was surprisingly discovered that the condenser for the second column can be bypassed and significant amounts of energy can be saved while still maintaining a high level of product purity. For example, greater than or equal to a 10% reduction in energy expended can be achieved with the present method, for example, greater than or equal to a 15% reduction in energy expended, for example, a greater than or equal to 20% reduction in energy expended.

Also disclosed herein is a method that can efficiently separate linear alpha olefins. The method can significantly reduce energy consumption, while maintaining product flow rate and product purity. Starting with a stream of light hydrocarbons such as butane, linear alkenes are often separated using a series of distillation columns. These separation processes present many engineering challenges. The narrow range of boiling points and relative volatilities of the components in the stream make separation by conventional distillation difficult and energy intensive. For example, separation from this stream is often accomplished using a sequence of two distillation columns in series. Each of the distillation columns in this sequence comprises both a reboiler and a condenser. With the method disclosed herein, energy consumption can be greatly reduced. For example, the method disclosed herein can reduce energy consumption by greater than or equal to 10%. The energy consumption reduction occurs in both the total condenser duty and the total reboiler duty. A high product flow rate and high product purity (e.g., 99.5 weight %) can also be maintained by the present method even at this lower energy level. The reduction in energy seen in the present method can also result in a 10% or greater reduction in total capital expenditure. Furthermore, it is noted that the present method can reduce the number of column condensers, further decreasing the overall capital expenditure.

In the present method, linear alpha olefin fractions can be separated using a sequence of two distillation columns in series, wherein the heaviest component can be withdrawn as a bottom product from each column. The method can include passing a feed stream through a column configuration comprising distillation columns. For example, the feed stream can be passed through a first distillation column. The feed stream can comprise hydrocarbons, for example, any combination of C4-C20 linear alpha olefins. For example, the source of the feed stream can be the product of a linear alpha olefin production process, for example, ethylene oligomerization. The feed stream can be a product of a C7−/C8+ separation column, for example, the feed stream can comprise C7− hydrocarbons or C8+ hydrocarbons. The feed stream can also comprise a solvent, for example, toluene, as well as spent catalyst particles and catalyst deactivating agents. For example, the feed stream can comprise C4 and C6 linear alpha olefins together with a solvent such as toluene. For example, the feed stream can comprise C8, C10, and C12+ linear alpha olefins.

A fraction "A" can be distributed to and withdrawn from a top portion of the first column. The fraction "A" can be passed through a condenser for the first column. The condenser can cool and partially condense at least a portion of the fraction "A". For example, the condenser can include a spiral heat exchanger and/or a plate heat exchanger. The condenser can utilize a stream of coolant fluid as a cooling means. A portion of the fraction "A" can be recycled back to the top portion of the first column. A fraction "C" can be distributed to and withdrawn from a bottom portion of the first column. The first column can comprise a reboiler. The reboiler can heat and partially vaporize at least a portion of the fraction "C". For example, the reboiler can include a spiral heat exchanger and/or a plate heat exchanger. The reboiler can utilize a stream of heating fluid as a heating means. A side steam can be withdrawn from a middle portion of the first column.

The first column can have 20 to 60 stages, for example, 30 to 50 stages, for example, 48 stages. The feed stream can enter the first column at a stage selected from, for example, 15 to 25, for example, at a stage selected from 19 to 24. A pressure within the first column can be 0 kiloPascals to 500 kiloPascals, for example, 20 kiloPascals to 450 kiloPascals, for example, a pressure within the top portion of the first column can be 400 kiloPascals. A temperature within the first column can be 50° C. to 300° C., for example, 100° C. to 200° C., for example, 160° C. [.] A mass reflux ratio for the first column can be 1 to 10, for example, 1.5 to 5, for example, 2 to 3, for example, 2.6. A condenser duty for the first column can be less than or equal to 3,000 kilowatts, for example, less than or equal to 2,500 kilowatts, for example, less than or equal to 2,000 kilowatts. A reboiler duty for the first column can be less than or equal to 2,000 kilowatts, for example, less than or equal to 1,500 kilowatts, for example, less than or equal to 1,000 kilowatts.

The feed flowrate to the first column can be 5,000 to 50,000 kilograms per hour (kg/hr), for example, 10,000 to 40,000 kg/hr, for example, 37,500 kg/hr. The fraction "A" flowrate from the top portion of the first column can be 2,500 to 60,000 kg/hr, for example, 3,000 to 55,000 kg/hr, for example, 52,000 kg/hr. The fraction "C" flowrate from the bottom portion of the first column can be 2,500 to 35,000 kg/hr, for example, 4,000 to 30,000 kg/hr, for example, 28,000 kg/hr. The side stream flowrate from the middle portion of the first column can be 2,500 to 8,500 kg/hr, for example, 3,500 to 6,500 kg/hr, for example, 6,000 kg/hr.

The side stream can be passed to a middle portion of a second distillation column. A recycle stream can be withdrawn from a top portion of the second column. The recycle stream can be passed to the top portion of the first column. The recycle stream can enter the first column at a stage above where the side stream is withdrawn from the first column. For example, the recycle stream can enter the first column at a stage selected from 5 to 15, for example, at a stage selected from 9 to 10.

A fraction "B" can be distributed to and withdrawn from a bottom portion of the second column. The side stream and/or the recycle stream can comprise a portion of the fraction "A" and/or the fraction "B". For example, the side stream can comprise 80% of fraction "B" by weight and 20% of fraction "A" by weight. The recycle stream can comprise 55% of fraction "B" by weight and 45% of fraction "A" by weight. The second column can comprise a reboiler. The reboiler can heat and partially vaporize at least a portion of the fraction "B". For example, the reboiler can include a spiral heat exchanger and/or a plate heat exchanger. The reboiler can utilize a stream of heating fluid as a heating means. A condenser is not present in the second column.

The second column can have 20 to 35 stages, for example, 25 to 30 stages, for example, 28 stages. The side stream can enter the second column at a stage selected from, for example, 10 to 20, for example, at a stage selected from 13 to 16. A pressure within the second column can be 0 kiloPascals to 750 kiloPascals, for example, 15 kiloPascals to 700 kiloPascals, for example, a pressure within the top portion of the second column can be 650 kiloPascals. A temperature within the second column can be 100° C. to 300° C., for example, 220° C. to 260° C., for example, 200° C. A reboiler duty for the second column can be less than or equal to 350 kilowatts, for example, less than or equal to 250 kilowatts, for example, less than or equal to 175 kilowatts.

The side stream flowrate to the second column can be 2,500 to 8,500 kg/hr, for example, 3,500 to 6,500 kg/hr, for example, 6,000 kg/hr. The recycle stream flowrate from the top portion of the second column can be 1,000 to 2,000 kg/hr, for example, 1,600 to 1,800 kg/hr, for example, 1,700 kg/hr. The fraction "B" flowrate from the bottom portion of the second column can be 2,000 to 5,000 kg/hr, for example, 2,200 to 4,500 kg/hr, for example, 4,250 kg/hr.

The carbon numbers of the fraction "A", the fraction "B", and the fraction "C" can be represented as follows: A<B<C (i.e., fraction "C" can be the heaviest component). The feed stream to the first column can be a product of a C7−/C8+ separation column, for example, the feed stream can comprise C7− hydrocarbons or C8+ hydrocarbons. When the feed stream comprises C7− hydrocarbons, the fraction "A" can comprise C4 hydrocarbons, the fraction "B" can comprise C6 hydrocarbons, the fraction "C" can comprise C7 hydrocarbons, or a combination comprising at least one of the foregoing. When the feed stream comprises C8+ hydrocarbons, the fraction "A" can comprise C8 hydrocarbons, the fraction "B" can comprise C10 hydrocarbons, the fraction "C" can comprise C12+ hydrocarbons, or a combination comprising at least one of the foregoing. The fraction "A", the fraction "B", the fraction "C", or a combination comprising at least one of the foregoing can have a purity of greater than or equal to 99.0%, for example, greater than or equal to 99.5%.

The present method can further comprise a second column configuration, for example, the second column configuration can be the same as the first column configuration. The first column configuration and the second column configuration can be in parallel. For example, the feed stream to first column configuration can comprise C7− hydrocarbons and a feed stream to the second column configuration can comprise C8+ hydrocarbons. A total reboiler/condenser duty for both column configurations can be less than or equal to 32,500 kilowatts, for example, less than or equal to 32,000 kilowatts, for example, less than or equal to 31,500 kilowatts.

The present method can further comprise passing the fraction A, the fraction B, the fraction C, or a combination comprising at least one of the foregoing to a wide range of downstream processes. The lower carbon numbers, 1-butene, 1-hexene and 1-octene can be used as comonomers in the production of polyethylene. High density polyethylene (HDPE) and linear low density polyethylene (LL-DPE) can use approximately 2-4% and 8-10% of comonomers, respectively. Another use of C$ to C8 linear alpha olefins can be for production of linear aldehyde via oxo synthesis (hydroformylation) for later production of short-chain fatty acid, a carboxylic acid, by oxidation of an intermediate aldehyde, or linear alcohols for plasticizer application by hydrogenation of the aldehyde. Another use of 1-hexene is the production of the linear aldehyde heptanal via hydroformylation (oxo synthesis). Heptanal can be converted to the short-chain fatty acid heptanoic acid or the alcohol heptanol. An application of 1-decene is in making polyalphaolefin synthetic lubricant base stock (PAO) and to make surfactants in a blend with higher linear alpha olefins.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 1:
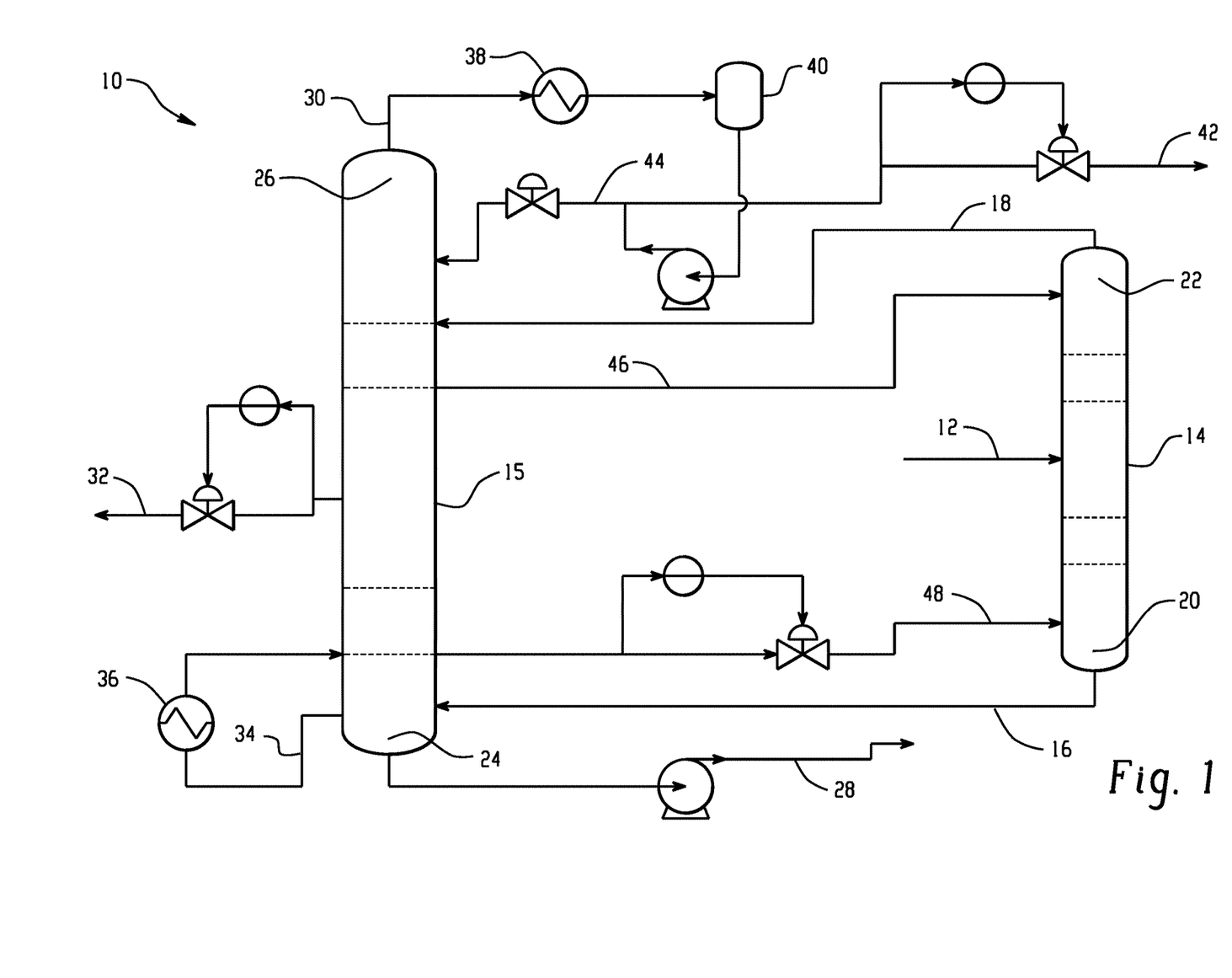
FIG. 1 is a schematic diagram representing a reactor scheme in a method of separating linear alpha olefins.

Referring now to FIG. 1, this simplified schematic diagram represents a reactor scheme 10 in a method for separating linear alpha olefins. The method can include passing a feed stream 12 through a first distillation column 14. For example, the feed stream 12 can comprise hydrocarbons, for example, C4-C20 linear alpha olefins. The source of the feed stream 12 can be the product of a linear alpha olefin production process, for example, ethylene oligomerization.

A C8− fraction 18 can be distributed to and withdrawn from a top portion 22 of the first column 14. The C8− fraction 18 can be passed directly from the top portion 22 of the first column 14 to a top portion 26 of a second distillation column 15. For example, the C8− fraction 18 can bypass a condenser and reflux drum for the first column 14. A C9+ fraction 16 can be distributed to and withdrawn from a bottom portion 20 of the first column 14. The C9+ fraction 16 can be passed directly from the bottom portion 20 of the first column 14 to a bottom portion 24 of the second distillation column 15. For example, the C9+ fraction 16 can bypass a reboiler for the first column 14.

A C10 fraction 32 can be withdrawn from the second distillation column 15 as a side draw. For example, the C10 fraction 32 can comprise decene. A bottom product, for example, a C11+ fraction 28, can be distributed to and withdrawn from a bottom portion 24 of the second distillation column 15. A reboiler stream 34 can be withdrawn from a bottom portion 24 of the second column 15. The reboiler stream 34 can be passed through a heat exchanger 36, for example, a reboiler 36. The reboiler stream 34 can then be recycled back to the bottom portion 24 of the second distillation column 15.

A top product, for example, a C8− fraction 30, can be distributed to and withdrawn from a top portion 26 of the second column 15. The C8− fraction 30 can be passed through a heat exchanger 38, for example, a condenser 38. The C8− fraction 30 can then be passed through a reflux drum 40. A portion of the C8− fraction 30 can be recycled back to a top portion 26 of the second distillation column 15 as a reflux stream 44. The remaining portion of the C8− fraction can be withdrawn as a product stream 42.

A liquid stream 46 can be recycled from a top portion 26 of the second column 15 back to a top portion 22 of the first column 14. A vapor stream 48 can be recycled from a bottom portion 24 of the second column 15 back to a bottom portion 20 of the first column 14.

Figure 2:
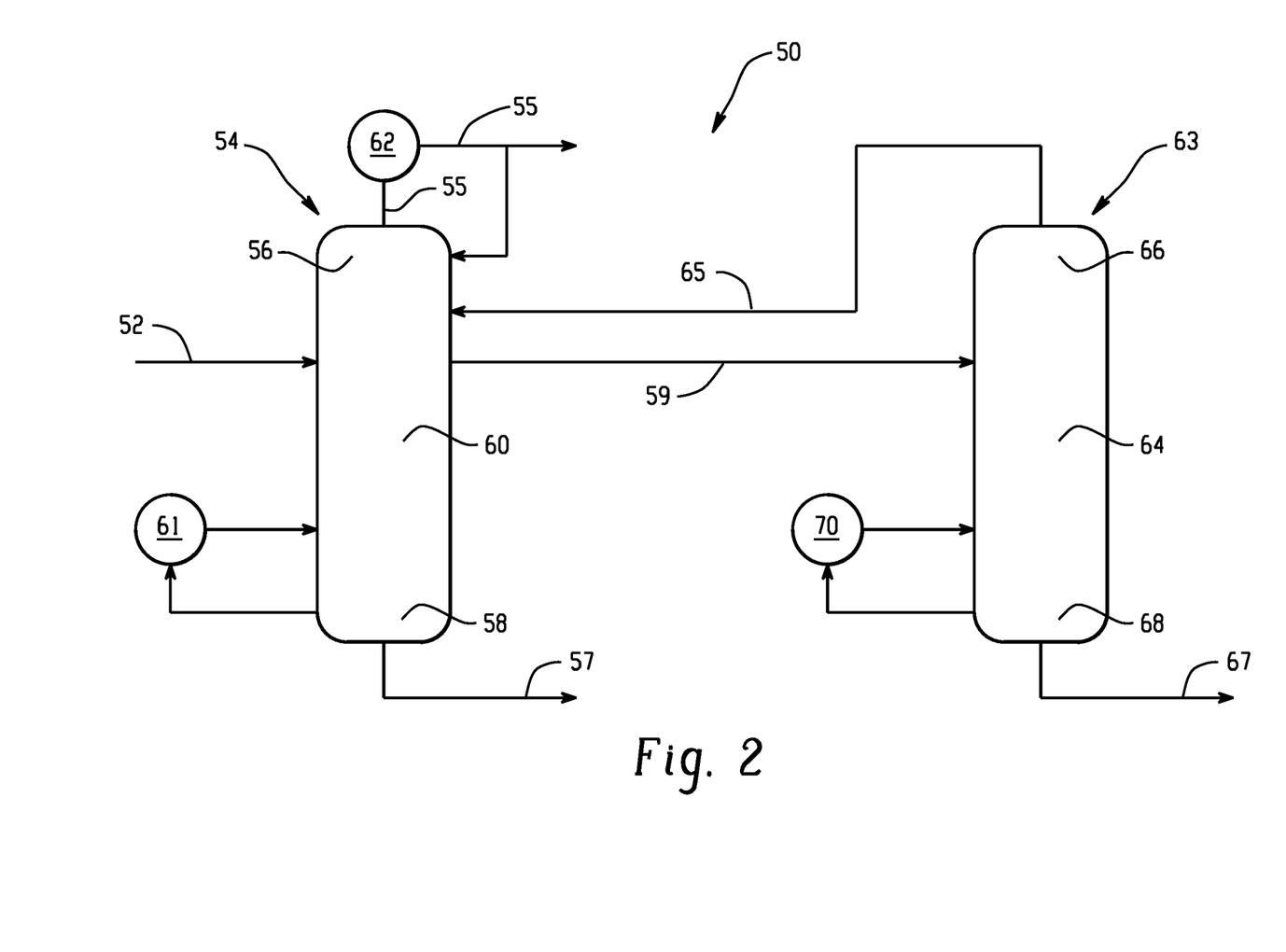
FIG. 2 is another schematic diagram representing a reactor scheme in a method of separating linear alpha olefins

Referring now to FIG. 2, this simplified schematic diagram represents a distillation column configuration 50 in a method for separating linear alpha olefins. The method can include passing a feed stream 52 through a first distillation column 54. The feed stream 52 can comprise hydrocarbons, for example, C4-C20 hydrocarbons, for example, C4 and C6 hydrocarbons and a solvent. The solvent can comprise toluene. The feed stream 52 can comprise hydrocarbons such as C8, C10, and C12+ hydrocarbons or a combination comprising at least one of the foregoing. The source of the feed stream 52 can be the product of a linear alpha olefin production process, for example, ethylene oligomerization.

A fraction "A" 55 can be distributed to and withdrawn from a top portion 56 of the first column 54. The fraction "A" 55 can be passed through a condenser 62 for the first column 54. A portion of the fraction "A" 55 can be recycled back to the top portion 56 of the first column 54.

A fraction "C" 57 can be distributed to and withdrawn from a bottom portion 58 of the first column 54. The first column 54 can comprise a reboiler 61. A side stream 59 can be withdrawn from a middle portion 60 of the first column 54. The side stream 59 can be passed to a middle portion 64 of a second distillation column 63.

A recycle stream 65 can be withdrawn from a top portion 66 of the second column 63. The recycle stream 65 can be passed to the top portion 56 of the first column 54. A fraction "B" 67 can be distributed to and withdrawn from a bottom portion 68 of the second column 63. The second column 63 can comprise a reboiler 70. The side stream 59 and/or the recycle stream 65 can comprise a portion of the fraction "A" 55 and/or the fraction "B" 67.

The following examples are merely illustrative of the method of separating linear alpha olefins disclosed herein and are not intended to limit the scope hereof. Unless otherwise stated, the examples were based upon simulations.

The following examples are merely illustrative of the method of separating linear alpha olefins disclosed herein and is not intended to limit the scope hereof.

EXAMPLES

Simulations are conducted using a steady state process model in ASPEN PLUS (commercial process engineering software). A detailed steady state process model is developed and the model is validated extensively using plant data. The validated model is used to analyze the performance of the modified distillation sequence. The data in Examples 1 and 2 is from both the validated plant data and the simulated model.

Example 1

A non-modified direct distillation sequence is simulated for the purposes of this example. The simulated model results are compared with the plant data and validated with the plant data. Decene is separated from a linear alpha olefin stream using a direct sequence of two distillation columns in series. Each of the distillation columns in this direct sequence comprises both a reboiler and a condenser. The conditions and results are presented in Table 1.

Example 2

A modified distillation sequence in accordance with the present disclosure is simulated for the purposes of this example. Decene is separated from a linear alpha olefin stream using a modified sequence of two distillation columns in series, as depicted in FIG. 1, wherein a reboiler and a condenser for the first column are bypassed (the first column does not comprise a reboiler or a condenser). The conditions and results are presented in Table 1.

As can be seen from Table 1, the present method (Example 2), as depicted in FIG. 1, achieves a greater than or equal to 20% energy reduction when compared to the non-modified sequence of Example 1. The present method can bypass the condenser and reboiler of the first column and significantly reduce condenser and reboiler duty for the process. In the present method, the second column can act as an additional gas-liquid contacting tray column that improves the separation of decene. For example, a significant increase in product purity, from 99.1 wt. % (Example 1) to 99.5 wt. % (Example 2), is also achieved by the present method. Bypass of the reboiler and condenser for the first column can facilitate a simple and more precise process of decene separation. For example, the present method can also achieve a 20% reduction in total capital costs.

Example 3

Simulations are conducted using a steady state process model in ASPEN PLUS (commercial process engineering software). Total condenser duty and total reboiler duty are reported in kilowatts (kw). Flow rate is reported in kilograms per hour (kg/hr) and pressure is reported in kiloPascals.

Example 3

Two column configurations in parallel are simulated for the purposes of this example. Each column configuration is in accordance with the column configuration 50 of FIG. 2. The feed stream to the first column configuration comprises c7− hydrocarbons and the feed stream to the second column configuration comprises c8+ hydrocarbons. The results and specifications are presented in table 2. The total reboiler duty is calculated as the sum of the reboiler duty for both distillation columns. The total condenser duty is the sum of the condenser duty for both columns.

Example 4

Two column configurations in parallel are simulated for the purposes of this example. Each column configuration differs from the column configuration 50 of FIG. 2 in that there are no recycle streams or side streams. Instead, the fraction withdrawn from the top portion of the second column is passed through a condenser. The feed stream to the first column configuration comprises C7− hydrocarbons and the feed stream to the second column configuration comprises C8+ hydrocarbons. The results and specifications

TABLE 1

Comparison of Distillation Conditions and Results

| | Comparative Example 1 | | | Example 2 | Energy |
| --- | --- | --- | --- | --- | --- |
| | First Column | Second Column | Total | Total | Savings |
| Stages | 33 | 31 | | 64 | |
| Condenser Duty (kw) | −931.42 | −676.33 | −1607.75 | −1283.44 | 20% |
| Reflux Ratio (mol/mol) | 2.46 | 2.92 | | 3.792 | |
| Reboiler Duty (kw) | 860 | 765 | 1625 | 1300 | 20% |
| Boil-up Ratio (mol/mol) | 1.786 | 2.565 | | 4.349 | |
| C10 Purity (wt. %) | | 0.991 | | 0.995 | |
| C10 Flow Rate (kg/hr) | | 2226 | | 2216 | |
| C10 Temp. (° C.) | | 176 | | 177 | |
| C11+ Temp. (° C.) | | 245 | | 245 | | are presented in Table 2. The total reboiler duty is calculated as the sum of the reboiler duty for both distillation columns. The total condenser duty is the sum of the condenser duty for both columns.

TABLE 2

Comparison of Separation Results

| Column specifications | First Column (C7−) | Second Column (C7−) | First Column (C8+) | Second Column (C8+) | Total |
|---|---|---|---|---|---|
| Example 3 | | | | | |
| Stages | 48 | 28 | 31 | 29 | — |
| Feed stage | 24 | 16 | 19 | 13 | — |
| Top stage pressure | 403.7 | 653.7 | 23.7 | 18.7 | — |
| Feed flow | 37555 | 5932 | 9452 | 4000 | — |
| Bottom flow | 28100.39 | 4257 | 4042 | 2210 | — |
| Top flow | 5197.65 | 1675 | 3199 | 1789 | — |
| Side stream flow | 5932 | — | 4000 | — | — |
| Mass reflux ratio | 2 | — | 2.6 | — | — |
| Condenser duty | −1822 | 0 | 971.5 | — | −31925.5 |
| Reboiler duty | 7432.5 | 288 | 838 | 169 | 31334.5 |
| Example 4 | | | | | |
| Stages | 48 | 28 | 31 | 29 | — |
| Feed stage | 24 | 16 | 19 | 13 | — |
| Top stage pressure | 403.7 | 653.7 | 23.7 | 18.7 | — |
| Feed flow | 37555 | 9399 | 9452 | 6264 | — |
| Bottom flow | 28089 | 4281 | 6264 | 4070 | — |
| Top flow | 9466 | 5096 | 3188 | 2194 | — |
| Mass reflux ratio | 1.367 | 0.6 | 2.3 | 3.14 | — |
| Condenser duty | −2705 | −787 | −885 | −702 | −36154 |
| Reboiler duty | 8388 | 1121.8 | 871 | 750 | 33737.8 |

As can be seen from Table 2, the present method (Example 3), as depicted in FIG. 2, achieves a greater than or equal to 10% reduction in total reboiler/condenser duty as compared to a method wherein the second column comprises a condenser (Example 4). Table 2 also shows that a high product flow rate can be maintained even at this lower energy level. The reduction in energy can also result in a 10% or greater reduction in total capital expenditure. The present method also utilizes two fewer condensers.

The methods disclosed herein include(s) at least the following aspects:

Aspect 1: A method of separating linear alpha olefins, comprising: passing a feed stream comprising linear alpha olefins through a first column; distributing a C8− fraction to a top portion of the first column; distributing a C9+ fraction to a bottom portion of the first column; passing the C8− fraction directly to a top portion of a second column; passing the C9+ fraction directly to a bottom portion of a second column; distributing a C11+ fraction to the bottom portion of the second column; withdrawing a C10 fraction as a side draw from the second column; and passing a liquid stream and a vapor stream from the second column to the first column.

Aspect 2: The method of Aspect 1, wherein the source of the feed stream is the product of an ethylene oligomerization process.

Aspect 3: The method of any of the preceding aspects, wherein the feed stream comprises C4 to C20 linear alpha olefins.

Aspect 4: The method of any of the preceding aspects, wherein the C10 fraction comprises decene.

Aspect 5: The method of Aspect 4, wherein the C10 fraction comprises greater than or equal to 99% decene.

Aspect 6: The method of Aspect 5, wherein the C10 fraction comprises greater than or equal to 99.5% decene.

Aspect 7: The method of any of the preceding aspects, wherein the first column does not comprise a reboiler or a condenser.

Aspect 8: The method of any of the preceding aspects, wherein no dividing wall is located between the first column and the second column.

Aspect 9: The method of any of the preceding aspects, comprising passing the liquid stream from the top portion of the second column to the top portion of the first column.

Aspect 10: The method of any of the preceding aspects, comprising passing the vapor stream from the bottom portion of the second column to the bottom portion of the first column.

Aspect 11: The method of any of the preceding aspects, wherein the second column comprises a reboiler and/or a condenser.

Aspect 12: The method of Aspect 11, wherein a reboiler duty for the second column is less than or equal to 1300 kilowatts.

Aspect 13: The method of Aspect 11, wherein the condenser duty for the second column is less than or equal to 1300 kilowatts.

Aspect 14: The method of Aspect 11, wherein a boil-up ratio for the second column is 4:1 to 5:1.

Aspect 15: The method of Aspect 11, wherein a reflux ratio for the second column is 3:1 to 4:1.

Aspect 16: The method of any of the preceding aspects, wherein a total amount of energy consumed by the method is reduced by greater than or equal to 20% as compared to a method wherein a first column comprises a reboiler and/or a condenser.

Aspect 17: The method of any of the preceding aspects, wherein the feed stream comprises ethylene.

Aspect 18: The method of any of the preceding aspects, further comprising withdrawing the C8− fraction from the top portion of the second column and withdrawing the C11+ fraction from the bottom portion of the second column.

Aspect 19: The method of any of the preceding aspects, further comprising passing the C8− fraction and/or the C11+ fraction through a third column.

Aspect 20: A method of separating linear alpha olefins, comprising: passing a feed stream comprising C4 to C20 linear alpha olefins and ethylene through a first column, wherein the first column does not comprise a reboiler or a condenser; distributing a C8− fraction to a top portion of the first column; distributing a C9+ fraction to a bottom portion of the first column; passing the C8− fraction directly to a top portion of a second column; passing the C9+ fraction directly to a bottom portion of a second column, wherein no dividing wall is located between the first column and the second column; distributing a C11+ fraction to the bottom portion of the second column; withdrawing a C10 fraction comprising greater than or equal to 99.5% decene as a side draw from the second column; and passing a liquid stream from the top portion of the second column to the top portion of the first column and passing a vapor stream from the bottom portion of the second column to the bottom portion of the first column; wherein a total amount of energy consumed by the method is reduced by greater than or equal to 20% as compared to a method wherein a first column comprises a reboiler and/or a condenser.

Aspect 21: A method of separating linear alpha olefins, comprising: passing a feed stream comprising linear alpha olefins through a column configuration, wherein passing the feed stream through the column configuration comprises: passing the feed stream through a first column; distributing a fraction A to a top portion of the first column; distributing a fraction C to a bottom portion of the first column; withdrawing a side stream from a middle portion of the first column; passing the side stream to a middle portion of a second column; withdrawing a recycle stream from a top portion of the second column; passing the recycle stream to the top portion of the first column; and distributing a fraction B to a bottom portion of the second column.

Aspect 22: The method of Aspect 21, wherein the source of the feed stream is the product of an ethylene oligomerization process and/or a C7−/C8+ separation column.

Aspect 23: The method of any of Aspects 21 or 22, wherein the feed stream comprises C4 to C20 linear alpha olefins.

Aspect 24: The method of any of Aspects 21-23, wherein the carbon numbers of the fraction A, the fraction B, and the fraction C are represented: A<B<C.

Aspect 25: The method of any of Aspects 21-24, further comprising withdrawing the fraction A from the top portion of the first column, withdrawing the fraction C from the bottom portion of the first column, withdrawing the fraction B from the bottom portion of the second column, or a combination comprising at least one of the foregoing.

Aspect 26: The method of Aspect 25, further comprising passing the fraction A, the fraction B, the fraction C, or a combination comprising at least one of the foregoing to a downstream polymerization process.

Aspect 27: The method of any of Aspects 21-26, wherein the second column does not comprise a condenser. Similarly the panels can be solid, hollow, or a combination thereof (e.g., can be multiwall panels wherein cavities of the panels are hollow and may optionally be filled, e.g., comprise a fluid (such as gas, liquid and/or gel)), depending on the desired properties of the structure (e.g., soundproof, heat transmission, light transmission, weight, etc.). For example, the panels can optionally be arranged so that there is a space between adjacent stacked panels (e.g., see FIGS. 15 and 18) or without space between the adjacent stacked panels (e.g., see FIG. 12), and the panels can be solid, hollow, and/or filled (with a fluid such as a liquid, gel, and/or gas), with a variety of rib configurations (e.g., see FIGS. 12, 15, and 18)

Aspect 28: The method of Aspect 27, wherein there is a greater than or equal to 10% reduction in total reboiler/condenser duty as compared to a method wherein the second column comprises a condenser, preferably, greater than or equal to 15%, more preferably, greater than or equal to 20%.

Aspect 29: The method of Aspect 27, wherein there is a greater than or equal to 10% reduction in capital expenditure as compared to a method wherein the second column comprises a condenser, preferably, greater than or equal to 15%.

Aspect 30: The method of any of Aspects 21-29, wherein a total reboiler/condenser duty for the column configuration is less than or equal to 32,500 kilowatts, preferably, less than or equal to 32,000 kilowatts, more preferably, less than or equal to 31,500 kilowatts.

Aspect 31: The method of any of Aspects 21-30, wherein the recycle stream enters the first column at a stage above where the side stream is withdrawn from the first column.

Aspect 32: The method of any of Aspects 21-31, wherein the recycle stream enters the first column at a stage selected from 5-15, preferably, at a stage selected from 9-10.

Aspect 33: The method of any of Aspects 21-32, wherein a carbon number of the side stream and/or the recycle stream is less than or equal to a carbon number of the fraction B.

Aspect 34: The method of any of Aspects 21-33, wherein the fraction A, the fraction B, the fraction C, or a combination comprising at least one of the foregoing has a purity of greater than or equal to 99.0%, preferably, greater than or equal to 99.5%.

Aspect 35: The method of any of Aspects 21-34, wherein the fraction A comprises C4 hydrocarbons, the fraction B comprises C6 hydrocarbons, the fraction C comprises C7 hydrocarbons, or a combination comprising at least one of the foregoing.

Aspect 36: The method of any of Aspects 21-35, wherein the fraction A comprises C8 hydrocarbons, the fraction B comprises C10 hydrocarbons, the fraction C comprises C12+ hydrocarbons, or a combination comprising at least one of the foregoing.

Aspect 37: The method of any of Aspects 21-36, further comprising a second column configuration, wherein the second column configuration is the same as the first column configuration.

Aspect 38: The method of Aspect 37, wherein the first column configuration and the second column configuration are in parallel.

Aspect 39: The method of Aspect 37, wherein the feed stream to first column configuration comprises C7− hydrocarbons and a feed stream to the second column configuration comprises C8+ hydrocarbons.

Aspect 40: A method of separating linear alpha olefins, comprising: passing a feed stream comprising linear alpha olefins through a column configuration, wherein passing the feed stream through the column configuration comprises: passing the feed stream through a first column; distributing a fraction A to a top portion of the first column; distributing a fraction C to a bottom portion of the first column; withdrawing a side stream from a middle portion of the first column; passing the side stream to a middle portion of a second column, wherein the second column does not comprise a condenser; withdrawing a recycle stream from a top portion of the second column; passing the recycle stream to the top portion of the first column; and distributing a fraction B to a bottom portion of the second column; wherein the carbon numbers of the fraction A, the fraction B, and the fraction C are represented: A<B<C; wherein the fraction A comprises C4 hydrocarbons, the fraction B comprises C6 hydrocarbons, the fraction C comprises C7 hydrocarbons, or a combination comprising at least one of the foregoing; wherein there is a greater than or equal to 10% reduction in total reboiler/condenser duty as compared to a method wherein the second column comprises a condenser, preferably, greater than or equal to 15%, more preferably, greater than or equal to 20%.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of separating linear alpha olefins, comprising:
    a. passing a feed stream comprising linear alpha olefins through a first column;
    b. distributing a C8− fraction to a top portion of the first column;
    c. distributing a C9+ fraction to a bottom portion of the first column;
    d. passing the C8− fraction directly to a top portion of a second column;
    e. passing the C9+ fraction directly to a bottom portion of a second column;
    f. distributing a C11+ fraction to the bottom portion of the second column;
    g. withdrawing a C10 fraction as a side draw from the second column; and
    h. passing a liquid stream and a vapor stream from the second column to the first column;
    wherein the C10 fraction comprises greater than or equal to 99% decene;
    wherein a pressure within the first column ranges from 0 kiloPascals to 1000 kiloPascals, and a temperature within the first column ranges from −100° C. to 300° C.;
    wherein a pressure within the second column ranges from 0 kiloPascals to 1000 kiloPascals and a temperature within the second column ranges from −100° C. to 300° C.;
    wherein the feed stream comprises C4-C20 linear alpha olefins;
    wherein a reboiler duty for the second column is less than or equal to 1300 kilowatts, wherein a condenser duty for the second column is less than or equal to 1300 kilowatts, wherein a boil-up ratio for the second column is 4:1 to 5:1, and wherein a reflux ratio for the second column is 3:1 to 4:1.

2. The method of claim 1, wherein a dividing wall is not present between the first column and the second column.

3. The method of claim 1, comprising passing the liquid stream from the top portion of the second column to the top portion of the first column and comprising passing the vapor stream from the bottom portion of the second column to the bottom portion of the first column.

4. The method of claim 1, wherein a total amount of energy consumed by the method is reduced by greater than or equal to 20% as compared to a method wherein a first column comprises a reboiler and/or a condenser.

5. The method of claim 1, wherein the first column comprises a reboiler.

6. A method of separating linear alpha olefins, comprising:
    a. passing a feed stream comprising linear alpha olefins through a first column;
    b. distributing a C8− fraction to a top portion of the first column;
    c. distributing a C9+ fraction to a bottom portion of the first column;
    d. passing the C8− fraction directly to a top portion of a second column;
    e. passing the C9+ fraction directly to a bottom portion of a second column;
    f. distributing a C11+ fraction to the bottom portion of the second column;
    g. withdrawing the C8− fraction from the top portion of the second column;
    h. withdrawing the C11+ fraction from the bottom portion of the second column;
    i. passing the C8− fraction and/or the C11+ fraction through a third column;
    j. withdrawing a C10 fraction as a side draw from the second column; and
    k. passing a liquid stream and a vapor stream from the second column to the first column;
    wherein the C10 fraction comprises greater than or equal to 99% decene;
    wherein a pressure within the first column ranges from 0 kiloPascals to 1000 kiloPascals, and a temperature within the first column ranges from −100° C. to 300° C.;
    wherein a pressure within the second column ranges from 0 kiloPascals to 1000 kiloPascals and a temperature within the second column ranges from −100° C. to 300° C.;

wherein the feed stream comprises C4-C20 linear alpha olefins
wherein a reboiler duty for the second column is less than or equal to 1300 kilowatts;
wherein a condenser duty for the second column is less than or equal to 1300 kilowatts;
wherein a boil-up ratio for the second column is 4:1 to 5:1; and wherein a reflux ratio for the second column is 3:1 to 4:1.

7. A method of separating linear alpha olefins, comprising passing a feed stream comprising linear alpha olefins through a column configuration, wherein passing the feed stream through the column configuration comprises:
  i. passing the feed stream through a first column;
  ii. distributing a fraction A to a top portion of the first column;
  iii. distributing a fraction C to a bottom portion of the first column;
  iv. withdrawing a side stream from a middle portion of the first column;
  v. passing the side stream to a middle portion of a second column;
  vi. withdrawing a recycle stream from a top portion of the second column;
  vii. passing the recycle stream to the top portion of the first column;
  viii. distributing a fraction B to a bottom portion of the second column;
  ix. withdrawing the fraction A from the top portion of the first column; and
  x. passing the withdrawn fraction A through a condenser for the first column forming a condensed fraction A;
wherein each of the fraction A, the fraction B and the fraction C comprise linear alpha olefins;
wherein the carbon numbers of the alpha olefins of the fraction A, the fraction B, and the fraction C are represented: A<B<C;
wherein at least one of the fraction A, the fraction B or the fraction C has a purity of greater than or equal to 99.0;
wherein the fraction A comprises C4 hydrocarbons, the fraction B comprises C6 hydrocarbons, the fraction C comprises C7 hydrocarbons, or a combination comprising at least two of the foregoing;
wherein a pressure within the first column ranges from 0 kiloPascals to 1000 kiloPascals, and a temperature within the first column ranges from −100° C. to 300° C.;
wherein a pressure within the second column ranges from 0 kiloPascals to 1000 kiloPascals and a temperature within the second column ranges from −100° C. to 300° C.;
wherein a reboiler duty for the second column is less than or equal to 1300 kilowatts;
wherein a condenser duty for the second column is less than or equal to 1300 kilowatts;
wherein a boil-up ratio for the second column is 4:1 to 5:1; and
  wherein a reflux ratio for the second column is 3:1 to 4:1.

8. The method of claim 7, further comprising withdrawing the fraction C from the bottom portion of the first column, withdrawing the fraction B from the bottom portion of the second column, or a combination thereof.

9. The method of claim 7, further comprising the step of recycling a portion of the condensed fraction A back to the top portion of the first column.

10. The method of claim 7, wherein the side stream from the middle portion of the first column comprises a portion of fraction A.

11. The method of claim 7, wherein the recycle stream from the top portion of the second column comprises a portion of fraction A.

12. The method of claim 7, further comprising a second column configuration, wherein the second column configuration is the same as the first column configuration, wherein the first column configuration and the second column configuration are in parallel, wherein the feed stream to the first column configuration comprises C7− hydrocarbons and a feed stream to the second column configuration comprises C8+ hydrocarbons.

13. The method of claim 7, wherein the first column comprises a reboiler.

* * * * *